United States Patent
Chen et al.

(10) Patent No.: US 8,652,216 B2
(45) Date of Patent: Feb. 18, 2014

(54) SELF DEPLOYING IMPLANT IN NEEDLE

(75) Inventors: Steve Chen, Westfield, IN (US); Ryan Dempsey, Westfield, IN (US); Jeffrey Miller, East Haven, CT (US); Amy Overby, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 565 days.

(21) Appl. No.: 12/938,474

(22) Filed: Nov. 3, 2010

(65) Prior Publication Data

US 2011/0093088 A1    Apr. 21, 2011

Related U.S. Application Data

(63) Continuation of application No. PCT/US2009/042200, filed on Apr. 30, 2009.

(60) Provisional application No. 61/049,938, filed on May 2, 2008.

(51) Int. Cl.
*A61F 2/02* (2006.01)

(52) U.S. Cl.
USPC ........................................ 623/23.72

(58) Field of Classification Search
USPC ........................................ 623/23.72
See application file for complete search history.

(56) References Cited

U.S. PATENT DOCUMENTS

| | | | |
|---|---|---|---|
| 4,511,653 A | 4/1985 | Play et al. | |
| 4,902,508 A | 2/1990 | Badylak et al. | |
| 4,956,178 A | 9/1990 | Badylak et al. | |
| 4,994,028 A | 2/1991 | Leonard et al. | |
| 5,116,357 A | * 5/1992 | Eberbach | 606/213 |
| 5,273,532 A | 12/1993 | Niezink et al. | |
| 5,326,350 A | * 7/1994 | Li | 623/23.72 |
| 5,554,389 A | 9/1996 | Badylak et al. | |

(Continued)

FOREIGN PATENT DOCUMENTS

| | | |
|---|---|---|
| WO | WO 98/22158 | 5/1998 |
| WO | WO 9825637 | 6/1998 |
| WO | WO 2007/011443 A | 1/2007 |

OTHER PUBLICATIONS

Heeschen C., et al., "Nicotine stimulates angiogenesis and promotes tumor growth and atherosclerosis," Nature Medicine 7 (2001), No. 7, 833-839.

(Continued)

*Primary Examiner* — Corrine M McDermott
*Assistant Examiner* — Son Dang
(74) *Attorney, Agent, or Firm* — Woodard, Emhardt, Moriarty, McNett & Henry LLP

(57) ABSTRACT

Described, in certain inventive embodiments, are unique devices and methods for introducing implants into soft tissue of a patient. One of these devices includes a tissue-penetrating member that is configured to pass in its entirety through a volume of patient tissue. The tissue-penetrating member has a leading end and a trailing end, and provides a receiving space for receipt of an implant body portion for carrying the implant body portion into the volume of patient tissue. The device also includes an implant that has an implant body portion removably received in the receiving space of the tissue-penetrating member. The implant body portion is configured for deployment from the receiving space in the volume of patient tissue so as to remain deployed there along a passageway traversed by the tissue-penetrating member.

20 Claims, 5 Drawing Sheets

(56) References Cited

U.S. PATENT DOCUMENTS

| | | | |
|---|---|---|---|
| 5,876,452 A * | 3/1999 | Athanasiou et al. | 623/23.72 |
| 5,993,844 A | 11/1999 | Abraham et al. | |
| 6,098,629 A | 8/2000 | Johnson et al. | |
| 6,099,567 A | 8/2000 | Badylak et al. | |
| 6,206,931 B1 | 3/2001 | Cook et al. | |
| 6,312,474 B1 * | 11/2001 | Francis et al. | 623/23.72 |
| 6,375,989 B1 | 4/2002 | Badylak et al. | |
| 6,415,796 B1 | 7/2002 | Conrad et al. | |
| 6,516,806 B2 * | 2/2003 | Knudson et al. | 128/897 |
| 6,530,896 B1 | 3/2003 | Elliott | |
| 6,899,105 B2 | 5/2005 | Krueger et al. | |
| 7,008,763 B2 * | 3/2006 | Cheung | 435/1.1 |
| 7,047,981 B2 | 5/2006 | Durgin | |
| 7,100,613 B2 * | 9/2006 | Conrad et al. | 128/897 |
| 7,185,657 B1 | 3/2007 | Johnson et al. | |
| 7,237,553 B2 | 7/2007 | Knudson et al. | |
| 2001/0054428 A1 * | 12/2001 | Knudson et al. | 128/898 |
| 2002/0147382 A1 | 10/2002 | Neisz | |
| 2003/0013989 A1 | 1/2003 | Obermiller et al. | |
| 2004/0020497 A1 * | 2/2004 | Knudson et al. | 128/898 |
| 2007/0031508 A1 | 2/2007 | Armstrong | |
| 2007/0098755 A1 | 5/2007 | Patel | |

OTHER PUBLICATIONS

Johnson C., et al., "Matrix Metalloproteinase-9 is Required for Adequate Angiogenic Revascularization of Ischemic Tissues: Potential Role in Capillary Branching," Circulation Research 94 (2004), No. 2, pp. 262-268.

* cited by examiner

SELF DEPLOYING IMPLANT IN NEEDLE

REFERENCE TO RELATED APPLICATIONS

This application is a continuation of International Application No. PCT/US2009/042200, filed Apr. 30, 2009, which claims the benefit of U.S. Provisional Application No. 61/049,938 filed May 2, 2008, each of which is hereby incorporated by reference.

BACKGROUND

The present invention relates generally to medical technology and in particular aspects to devices and methods for introducing implants into patient tissue for augmentation and other purposes.

As further background, plastic surgery, including soft tissue augmentation, is a viable option for people who want to change their physical appearance. An increasingly popular form of plastic surgery is lip augmentation, a procedure to increase the fullness of the lips. Lips are augmented using a variety of techniques and materials. While some procedures offer a temporary fix, others provide a more permanent solution. Temporary lip augmentation often involves injecting a filler material into a lip, such as fat, collagen, hyaluronic acid, and particulated dermis or fascia.

Permanent lip augmentation eliminates or reduces some of the problems associated with temporary lip augmentation. One permanent lip augmentation technique involves injecting liquid silicone into the lip. However, liquid silicone is inherently difficult to remove from the lips should a problem arise or the patient desire removal. Further, liquid silicone injections carry a relatively high incidence of inflammation, migration, and even skin ulceration, which can occur many years later. Currently, liquid silicone is not FDA-approved for soft tissue augmentation, although it is still used outside the United States.

Other permanent lip augmentation techniques involve implanting various forms of expanded polytetrafluoroethylene (PTFE) into the lip, such as Gore-Tex™ strips or Softform™ and Ultrasoft™ tubes. PTFE is porous to allow tissue ingrowth into the material, which in turn, prevents migration.

Apart from procedures involving fillers or implants, other surgical procedures, such as lip rolls, lip lifts, and micro pigmentation, and nonsurgical techniques, such as using lip pumps, have been used to try to enhance the lips.

In addition to augmenting lips, a variety of other procedures for altering the appearance of patient physical features are commonly undertaken, particularly in the facial area. These include, as illustrative examples, procedures to diminish or otherwise improve the appearance of wrinkles and/or nasal labial folds on the face.

There remain needs for improved and/or alternative devices for introducing implants into patient tissue, as well as methods for manufacturing and using the same. The present invention is addressed to those needs.

SUMMARY

The present invention provides, in certain aspects, unique devices for introducing implants into soft tissue. Some of these devices involve a needle or other tissue-penetrating member that is configured to pass through a volume of patient tissue, and in so passing, to leave behind an implant that was carried into the tissue in a lumen or other open space in the member. The implant may be caused or allowed to exit the member in a variety of manners. While not necessary to broader aspects of the invention, in some cases, an implant will be configured for deployment from a needle lumen in a non-ejecting fashion such as in instances where the implant is drawn from the lumen. Illustratively, an implant can have a particular shape or otherwise be provided with means for anchoring itself at a bodily location as the implant delivery member is withdrawn over the implant and removed from the body.

One illustrative inventive device includes a tissue-penetrating member and an implant. The tissue-penetrating member is configured to enter a volume of patient tissue through an entry point, and to exit this same volume of patient tissue through an exit point that is spaced from the entry point. The tissue-penetrating member has a leading end and a trailing end, and provides a receiving space for receipt of an implant body portion for carrying the implant body portion into the volume of patient tissue. The implant has an implant body portion that is removably received in the receiving space of the tissue-penetrating member. The implant body portion is configured for deployment from the receiving space in the volume of patient tissue so as to remain deployed there along a passageway traversed by the tissue-penetrating member.

In another embodiment, the invention provides a method for introducing an implant into a volume of patient tissue. In this method, an implant deployment device is provided that includes a tissue-penetrating member and an implant. The tissue-penetrating member has a leading end and a trailing end, and provides a receiving space for receipt of an implant body portion. The implant has an implant body portion that is removably received in the receiving space of the tissue-penetrating member. As part of this method, the tissue-penetrating member is passed through a volume of patient tissue by causing it to enter the volume of patient tissue through an entry point, and exit the volume of patient tissue through an exit point that is spaced from the entry point. As part of this passing, the implant body portion is located in the volume of patient tissue in the receiving space of the tissue-penetrating member, and is deployed from the receiving space in the volume of patient tissue such that it remains deployed there along a passageway traversed by the tissue-penetrating member. Illustratively, the implant body portion can be carried into the volume of patient tissue in the receiving space of the tissue-penetrating member, or alternatively, the implant body portion can be inserted into the receiving space after the tissue-penetrating member has been located in the tissue.

One aspect of the present invention provides a device for introducing an implant into soft tissue of a patient. This device includes a tissue-penetrating member and an implant. The tissue-penetrating member is configured to pass in its entirety through a volume of patient tissue, and has a lumen that communicates with a trailing open end. The lumen is configured for receipt of an implant body portion for carrying the implant body portion into the volume of patient tissue. The implant has an implant body portion that is removably received in the lumen of the tissue-penetrating member. The implant body portion is suitable for deployment from the lumen in the volume of patient tissue, and through the trailing open end such that it remains deployed in the volume of patient tissue along a passageway traversed by the tissue-penetrating member.

Another aspect of the invention provides a method for introducing an implant into a volume of patient tissue. In this method, an implant deployment device is provided that includes a tissue-penetrating member and an implant. The tissue-penetrating member has a lumen that communicates with a trailing open end and is configured for receipt of an implant body portion. The implant has an implant body portion that is removably received in the lumen of the tissue-penetrating member. As part of this method, the tissue-penetrating member is passed in its entirety through a volume of patient tissue. In so passing, the implant body portion is carried into the volume of patient tissue in the lumen of the tissue-penetrating member. Additionally, the implant body portion is deployed from the lumen in the volume of patient tissue and through the trailing open end such that it remains deployed there along a passageway traversed by the tissue-penetrating member.

A further embodiment of the invention provides a method for introducing an implant into a volume of patient tissue. In this method, an implant deployment device is provided that includes a tissue-penetrating member and an implant. The tissue-penetrating member has a lumen that communicates with a trailing, open end. The implant is partially received through the trailing open end, and includes an implant body portion and an enlarged head portion. The implant body portion is removably positioned in the lumen of the tissue-penetrating member. The enlarged head portion extends from the implant body portion, and is sized and shaped for inhibiting passage of the enlarged head portion through the volume of patient tissue. As part of this method, the tissue-penetrating member is inserted into the volume of patient tissue through an entry point such that the implant body portion is carried into the volume of patient tissue. As another part of this method, the tissue-penetrating member is forced out of the volume of patient tissue through an exit point that is spaced from the entry point. In so forcing the tissue-penetrating member, the enlarged head portion makes contact with patient tissue that is adjacent the entry point. This contact is effective to anchor the implant in the volume of patient tissue such that the implant body portion is drawn from the lumen as the trailing open end is forced away from the entry point.

Other objects, embodiments, forms, features, advantages, aspects, and benefits of the present invention shall become apparent from the detailed description and drawings included herein.

DETAILED DESCRIPTION

Figure 1:
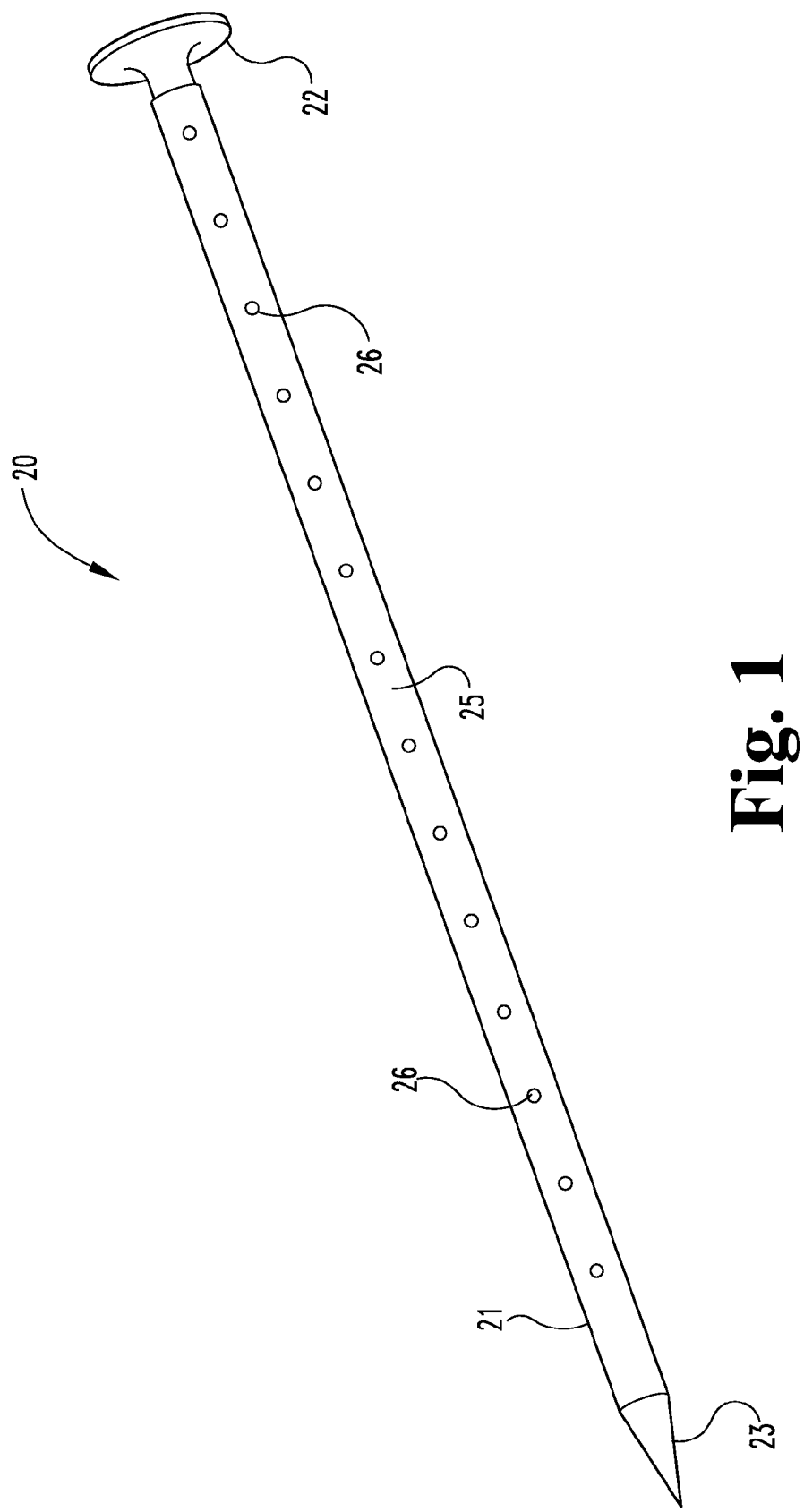
FIG. 1 is a perspective view of an implant deployment device according to one embodiment of the present invention.

While the present invention may be embodied in many different forms, for the purpose of promoting an understanding of the principles of the present invention, reference will now be made to the embodiments illustrated in the drawings, and specific language will be used to describe the same. It will nevertheless be understood that no limitation of the scope of the invention is thereby intended. Any alterations and further modifications in the described embodiments and any further applications of the principles of the present invention as described herein are contemplated as would normally occur to one skilled in the art to which the invention relates.

As disclosed above, in certain aspects, the present invention provides unique devices and methods for introducing implants into soft tissue of a patient. One of the devices includes a tissue-penetrating member that is configured to pass in its entirety through a volume of patient tissue. The tissue-penetrating member has a leading end and a trailing end, and provides a receiving space for receipt of an implant end, for carrying the implant body portion into the volume of patient tissue. The device also includes an implant that has an implant body portion removably received in the receiving space of the tissue-penetrating member. The implant body portion is configured for deployment from the receiving space in the volume of patient tissue so as to remain deployed there along a passageway traversed by the tissue-penetrating member.

With reference now to FIG. 1, shown is an implant deployment device 20 according to one embodiment of the present invention. Device 20 includes a tissue-penetrating member 21 and an implant 22. Tissue-penetrating member 21 has a leading end 23 and a trailing, open end 24. Leading end 23 includes a tapered portion that provides a tissue-penetrating tip. A generally cylindrical wall 25 extends between the leading end and the trailing end of member 21, and in this specific illustrative embodiment, multiple openings 26 (optional) extend through the wall. Member 21 additionally provides a lumen, which communicates with trailing, open end 24. This lumen is configured for receipt of all or part of an implantable object for carrying the object into patient tissue, or for receipt of an implantable object once it has been located in patient tissue. Accordingly, an implant such as implant 22 can be partially received through trailing, open end 24 as shown in FIG. 1.

Tissue-penetrating member 21 may be formed with any suitable material to enable it to be used in accordance with the present invention. These materials include some that are metallic and some that are non-metallic. Those skilled in the art will recognize a large variety of suitable materials, and therefore, they are encompassed by the present invention. A particular material may be selected to take advantage of one or more of its properties such as but not limited to its weight, durability, rigidity, etc. In this regard, a member, or any portion thereof, may be rigid, malleable, semi-flexible, or flexible.

Suitable materials from which to construct tissue-penetrating members include but are not limited to stainless steel, titanium, cobalt, tantalum, gold, platinum, nickel, iron, copper and the like, as well as alloys of these metals (e.g., cobalt alloys, such as Elgiloy®, a cobalt-chromium-nickel alloy, MP35N, a nickel-cobalt-chromium-molybdenum alloy, and Nitinol®, a nickel-titanium alloy). Additionally or alternatively, the member can include material in the form of yarns, fibers, and/or resins, e.g., monofilament yarns, high tenacity polyester, and the like. A member can also include other plastic, resin, polymer, woven, and fabric surgical materials, other conventional synthetic surgical materials, such as a shape-memory plastic, and/or combinations of such materials. Further, appropriate ceramics can be used, including, without limitation, hydroxyapatite, alumina and pyrolytic carbon.

Tissue-penetrating members useful in the invention can be generally straight or non-straight. In certain aspects, one or more parts of a tissue-penetrating member will be curvilinear, bent, or otherwise suitably shaped. Illustratively, a member may be curved to a degree along its entire length. In some forms, a member will be composed of a somewhat malleable material such as but not limited to a woven or spirally-configured metal or alloy material, or a plastic (hydrocarbonbased) material, which may be bent to a desirable angle or curvature. If desirable, the shape of such a member may be adjusted at certain intervals in a procedure.

As well, tissue-penetrating members such as tissue-penetrating member 21 may be formed of a single, integral body, or alternatively, from multiple connected pieces. The tissue-penetrating tip is desirably of the non-coring type, and in certain embodiments, can include a closed tip such as a trocar tip having multiple facets, e.g. two, three or four facets, a smooth pencil tip, a blunt tip, a bullet tip (e.g. non-cutting) or any other suitable tip for forming a tract through soft tissue and/or for traversing an existing tract such as one formed by another surgical instrument. These or other penetrating tips can be formed upon or added to the end of a cannulated or other member body portion in accordance with the invention using techniques such as welding, swaging, grinding, and/or any other suitable method.

Figure 2:
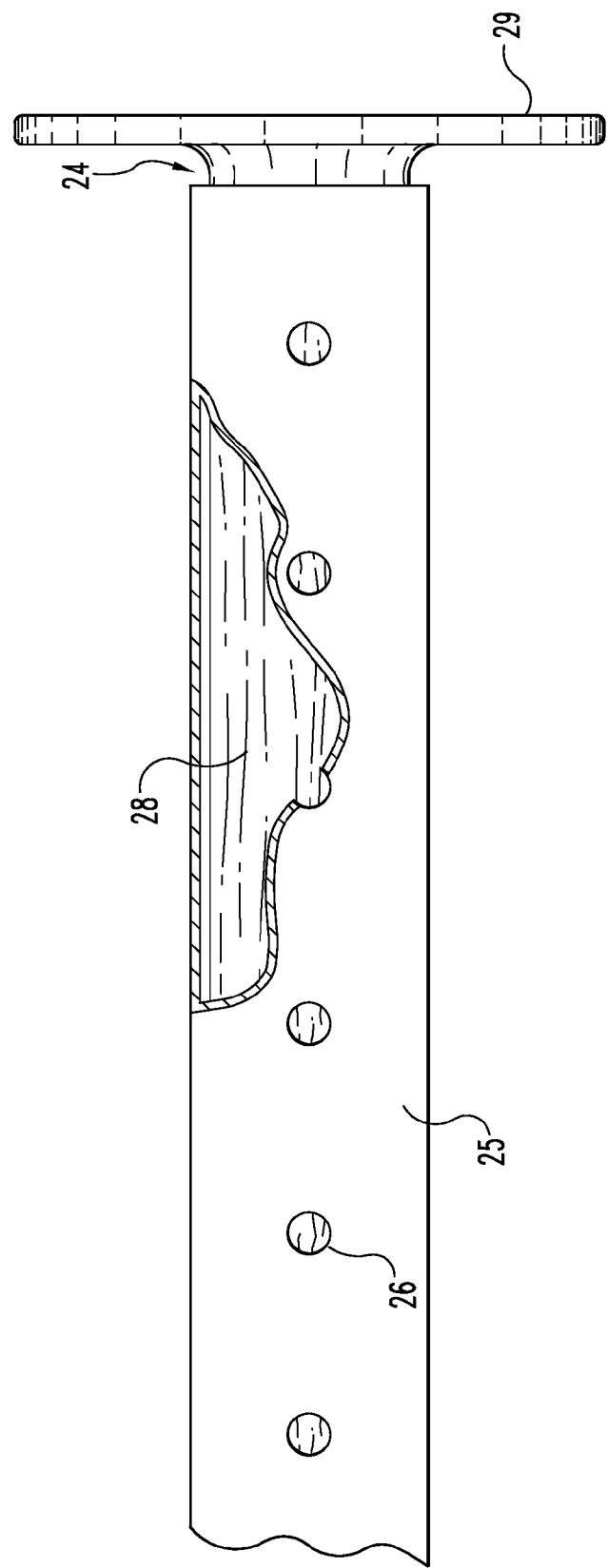
FIG. 2 provides an enlarged, partial view of the device of FIG. 1.

Referring now to FIG. 2, shown is an enlarged, partial view of device 20. Implant 22 includes a generally cylindrical implant body portion 28 at least part of which can be removably positioned in the tissue-penetrating member lumen as shown. While not necessary to broader aspects of the invention, an implant body portion such as that presently shown may fill all or substantially all of the lumen. Additionally, the lumen itself may extend substantially the entire length of the member, or alternatively, along only a fraction of the member. Implant 22 also includes an enlarged head portion 29, which extends from implant body portion 28. As disclosed in more detail below, an enlarged portion of this sort, in some forms, can be effective to prevent, or at least inhibit, the enlarged head portion from passing into and/or through a space traversed by tissue-penetrating member 21.

Implants useful in the present invention can exhibit a variety of shapes and sizes. Thus, while the implant body portion 28 in this specific illustrative embodiment is generally cylindrical, many other suitably shaped implant body portions are contemplated as within the scope of the present invention. These include various sheet form bodies and non-sheet form bodies, any of which can be adapted to suit a particular tissue augmentation or restoration procedure, technique or patient. When generally cylindrical, an implant body portion can, for example, have a diameter of about 0.5 mm to about 25.0 mm and a length of about 0.5 cm to about 30 cm, although larger or smaller values for these dimensions could be used in accordance with the invention. Thus, an implant in some forms of the invention will include a portion that is generally cylindrical, and has a diameter ranging from about 1.0 mm to about 8.0 mm, more typically from about 1.5 mm to about 4.0 mm, and a length ranging from about 2.0 cm to about 18.0 cm, more typically from about 4.0 cm to about 12.0 cm. As well, an implant body portion such as that shown in FIG. 1 may be formed with one or more of a variety of biocompatible materials including some that are naturally derived and some that are non-naturally derived. Although not necessary to broader aspects of the invention, in certain forms, an implant body will include an at least somewhat stabilized mass of collagenous material, for example, a mass that includes rolled and/or folded layers of a sheet-form collagenous extracellular matrix (ECM) material that have been dried under compression. Some preferred implants, or portions thereof, will be formed with a remodelable, angiogenic material, for example, a sheet-form remodelable ECM material such as submucosa.

An implant body can have a constant or varying cross-sectional area along its length. Illustratively, an implant body, or any portion thereof, can exhibit a generally cylindrical shape, a conical shape or any other suitable shape including some that have tapered and/or non-tapered longitudinal portions. As well, a cross section of a particular portion of an implant body can exhibit a variety shapes including some that have rectilinear and/or curvilinear features. Thus, an implant body can include a portion having a generally circular or non-circular (e.g., elliptical, square, star-shaped, hexagonal, etc.) cross section.

Additionally or alternatively, an implant body can include various other three-dimensional volumetric body portions such as but not limited to braids, tubes, hemi-cylinders, strands, threads, strips, pieces, slabs, wedges, blocks and other shaped body portions having suitable dimensions. In certain aspects, the size and shape of an implant body portion will be adapted to suit an unevenness or irregularity in the size and shape of a patient's lips, possibly resulting from a birth defect, accident, or trauma. In some forms, an implant will include a sheet-form body portion that is highly pliable such that it is deformable from the sheet form to a more three-dimensional form, such as a generally cylindrical form, upon impingement by soft tissues defining the passage into which the implant body is being placed. Such deformation of the sheet-form segment can occur by any suitable action, including for example rolling, gathering, folding, twisting, etc. of the sheet-form segment. Highly pliable non-sheet form implants may be employed in the present invention as well.

The implant bodies and other implant components described herein can be formed in any suitable manner including but not limited to by extrusion, using a mold or form, construction around a mandrel, and/or combinations or variations thereof. In some embodiments, an implant body is formed with a reconstituted or otherwise reassembled ECM material. Implant bodies can also be formed by folding or rolling, or otherwise overlaying one or more portions of a biocompatible material, such as a biocompatible sheet material. The overlaid biocompatible sheet material can be compressed and dried or otherwise bonded into a volumetric shape such that a substantially unitary construct is formed. In some forms, an inventive implant component is constructed by randomly or regularly packing one or more pieces of single or multilayer ECM sheet material within a mold and thereafter processing the packed material.

Methods for forming implant bodies useful in the invention can involve manipulating a material within a mold or form. It should be noted that this material may or may not be hydrated when placed in, on, around, etc. the mold or form. In some methods, a substantially dry ECM material (e.g., a powder or sheet material) can be placed in a mold and then suitably hydrated for further processing. In other methods, a hydrated starting material is placed in and/or on a mold or forming structure for further processing. For example, one or more hydrated sheets of ECM material can be applied to a form, e.g., wrapped at least partially around a mandrel so that portions of the sheet(s) overlap. Then, the one or more sheets can be dried, and in some embodiments, dried while under compression, to form a unitary implant body.

In some modes of formation, a hydrated graft material is provided within a single- or multiple-part mold having a plurality of apertures or holes extending through a wall of the mold, thereby providing access to the mold interior from an external location. These apertures can serve to enhance drying of a hydrated material during a processing step and in processes exerting vacuum pressure at these apertures, can promote and/or facilitate formation of surface protuberances on the graft material as portions of the same are drawn toward the apertures while under vacuum. In one aspect, an amount of ECM material is retained in such a mold, and needles or other material-displacing objects are inserted through some or all of the mold apertures and a distance into the ECM material, thereby displacing volumes of the ECM material. This can be performed when the graft material is hydrated, partially hydrated or dehydrated. In some forms, with needles inserted in a hydrated ECM material and providing passages therein, the material is subjected to conditions (e.g., freezing and/or dehydrating conditions) which, alone or in combination with one or more other conditions, cause or allow the passages to be generally retained in the ECM material after the needles are removed.

In one embodiment, one or more sheets of hydrated ECM material are suitably wrapped and/or randomly packed around a mandrel, and then a mold having a plurality of holes extending through a wall of the mold is placed around the material-covered mandrel, for example, so that an amount of pressure is placed on the ECM material. The mandrel can then optionally be removed. Thereafter, needles or other material-displacing objects are inserted through some or all of the holes and at least partially through the ECM material, thereby displacing volumes of the ECM material. The ECM material is then at least partially dried. In some aspects, a suitable lyophilization technique is employed, e.g., one with or without a pre-freezing step as described herein. In these or other drying methods in which needles or other penetrating elements are to be left within the mass during drying, these elements can optionally be provided with a plurality of apertures or holes or can otherwise be sufficiently porous to facilitate the drying operation by allowing the passage of hydrate from the wet mass. In one embodiment, a hydrated ECM material with emplaced needles can be subjected to freezing conditions so that the material and any contained hydrate become substantially frozen. Thereafter, the needles can be removed from the ECM material, and the remaining construct (with the frozen material passages substantially retaining their shape) can be placed under a vacuum so that the frozen hydrant sublimes from the material, thereby resulting in a dry implant body with retained passages therein.

In other modes of operation, passage-forming structures can be incorporated integrally into a mold so that passageways are formed upon introducing the starting material in and/or on the mold. In these aspects, the passage-forming structures can be part of the mold (e.g., extend from a surface of the mold), or they can be separate objects attached or otherwise coupled to the mold, to provide the desired passage or passages through the ultimately-formed implant body.

Although not necessary to broader aspects of the invention, in some aspects, the formation of such an implant body comprises wrapping one or more sheets of hydrated graft material around a mandrel a number of times. The resulting roll of graft material is then introduced into a mold, and the mandrel is removed (optional), e.g., before or after applying the mold. Thereafter, multiple material-displacing objects such as but not limited to needles are forced through apertures in the mold and into the hydrated graft material, and the material is subjected to one or more drying techniques such as a lyophilization process. In other aspects, the formation of such an implant body includes placing a flowable graft material into a mold and then subjecting the graft material to further processing. For example, a flowable ECM material mass, such as a gel, paste or putty, potentially incorporating a particulate ECM material, can be placed into a mold, and then with volumes of material displaced in the mass (e.g., by penetrating needles), the ECM material can be dried or otherwise caused to form an integral piece to provide an implant body having passages therein. Illustratively, each of the passages can be provided by forcing a single object through the material mass, or alternatively, where a mandrel is left in place to form a longitudinal lumen, by forcing two objects into the mass and toward one another from opposite directions until they abut the mandrel. The mass can then be processed to a solid implant body as discussed herein.

In certain aspects, an implant includes a material receptive to tissue ingrowth. Upon deployment of such an implant in accordance with the present invention, cells from the patient can infiltrate the material, leading to, for example, new tissue growth on, around, and/or within the implant. In some embodiments, the implant comprises a remodelable material. In these embodiments, the remodelable material promotes and/or facilitates the formation of new tissue, and is capable of being broken down and replaced by new tissue in such a way that the filling of a space by a deployed implant is maintained throughout the remodeling process so as to eventually fill the space with new tissue.

Remodelable ECM materials having a relatively more open matrix structure (i.e., higher porosity) are capable of exhibiting different material properties than those having a relatively more closed or collapsed matrix structure. For example, an ECM material having a relatively more open matrix structure is generally softer and more readily compliant to an implant site than one having a relatively more closed matrix structure. Also, the rate and amount of tissue growth in and/or around a remodelable material can be influenced by a number of factors, including the amount of open space available in the material's matrix structure for the infusion and support of a patient's tissue-forming components, such as fibroblasts. Therefore, a more open matrix structure can provide for quicker, and potentially more, growth of patient tissue in and/or around the remodelable material, which in turn, can lead to quicker remodeling of the material by patient tissue.

In this regard, any part of an implant used in the invention can have a level or degree of porosity. In certain embodiments, the porosity of a layer of ECM material is lowered by drying the material under compression. In general, compressing a pliable open matrix material, such as a pliable ECM material, increases the material's bulk density and decreases the material's porosity by decreasing the size of the voids in the open matrix. As is the case in certain aspects of the invention, when such a material is dried while being compressed, particularly under vacuum pressing conditions, the open matrix structure can become somewhat fixed in this relatively higher bulk density, lower porosity state (i.e., in a relatively more collapsed state). It should be noted that different compressing and drying techniques and/or methods, including different degrees of compressing and drying, can be designed through routine experimentation so as to allow for a material layer having an optimal degree of material bulk density and/or porosity for a particular application or procedure.

In certain aspects, an implant used in the invention includes at least two regions exhibiting differing biological, mechanical and/or other properties. Such differing regions (e.g., regions having differing porosities) can be established in certain locations, for example, locations providing a particular arrangement or pattern on and/or within the implant, and in some forms, such differing regions are formed by subjecting the implant to a suitable differential drying process. Illustratively, an implant can be configured so that regions configured to reside in one part of a tissue passage occupy a more open porosity region, while regions configured to reside in another part of the passage (e.g., in and/or around an opening into the passage) occupy more diminished porosity regions.

Figure 3A:
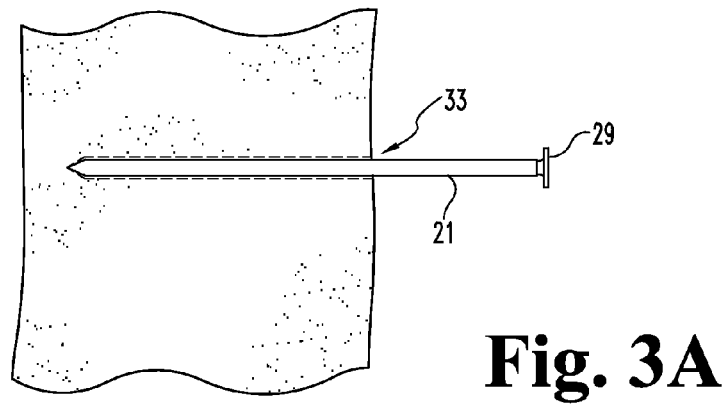
FIGS. 3A-3C show the implant deployment device of FIG. 1 being used to carry out parts of one illustrative inventive method.
Figure 3B:
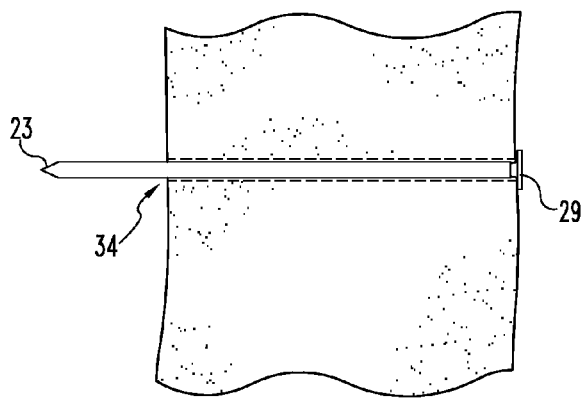
Figure 3C:
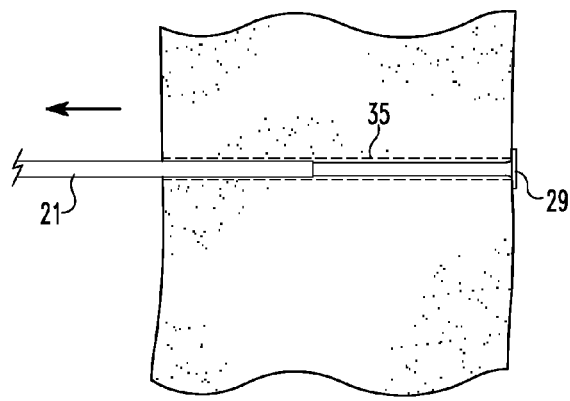

Device 20 can be utilized for a variety of medical purposes. With reference now to FIGS. 3A-3C, depicted are steps of one illustrative inventive method in which device 20 is so used. In one step and referring now to FIG. 3A, tissue-penetrating member 21 is inserted into a volume of patient tissue through an entry point 33 such that implant body portion 28 is carried into the volume of patient tissue in the tissue-penetrating member lumen. In this way, tissue-penetrating member wall 25 may be useful to provide a barrier between the implant and contaminants which may be present at the implantation site such as bacteria or cells located on outer surfaces of the patient's skin or on other non-sterile surfaces or objects. Any number of preparation steps can be taken prior to inserting tissue-penetrating member 21 into the volume of patient tissue. For example, tissue including entry point 33 and exit point 34 can receive sterilization treatment, local anesthesia, etc. Preparation steps can also be taken with regard to device 20. Illustratively, lubrication, wetting agents, antibiotics and other suitable ointments and substances can be applied to the device.

Implant deployment devices such as that depicted in FIG. 3A-3C, are particularly well suited to deploy an implant in human facial tissue and in particular a human lip. Nonetheless, it should be understood that such an implant deployment device could be used and if need be adapted for any augmentation or restoration procedure, technique, situation or patient. For example, implant deployment device 20 could be used to treat skin wrinkles, furrows, skin depressions, including depressed scars, nasal labial folds, and the like, as well as other tissue defects or deformations, e.g., those associated with aging, birth defects, accidents, trauma, etc. As well, the volume of patient tissue may be located at various places in the body. Illustratively, the volume of patient tissue may include all or part of a human upper lip. In other embodiments, the volume of patient tissue may comprise a lower lip, forehead, cheek, eyelid, ear, throat, neck, chin, nose, nasal labial fold, scalp, hand, arm, foot, ankle, leg, buttocks, abdomen, shoulder, back, breast or any other part of a patient in which an implant can be deployed.

In another step and referring now to FIG. 3B, tissue-penetrating member 21 is advanced further through the volume of patient tissue until it is forced out of the tissue through an exit point 34, which is spaced from entry point 33. Depending on factors such as the length of tissue-penetrating member 21, the distance between entry point 33 and exit point 34, the extent to which implant body portion 28 is received in the tissue-penetrating member lumen, etc., enlarged head portion 29 may or may not be in contact with the volume of patient tissue when leading end 23 exits the tissue.

Referring now to FIG. 3C, with enlarged head portion 29 making contact with tissue around entry point 33, tissue-penetrating member 21 can be advanced further through the volume of patient tissue. In some preferred embodiments, as the trailing end of the tissue-penetrating member is forced away from entry point 33 (in the direction of the arrow shown), this contact will be effective to anchor implant 22 in the volume of patient tissue such that implant body portion 28 is drawn from the tissue-penetrating member lumen through trailing, open end 24. Tissue-penetrating member 21 can then be fully removed from the volume of tissue and discarded, leaving at least part of implant body portion 28 in the tissue so as to remain there along a passageway 35 traversed by the tissue-penetrating member. As desired, one or more additional steps can then be taken to further the deployment procedure. Illustratively, portions of implant body portion 28 can be trimmed off or otherwise manipulated. Some forms of the implant will have a detachable enlarged head portion which can then be detached and discarded. An antibiotic ointment can be applied to the punctures at the entry and exit points to reduce the risk of infection. A bandage, or possibly even sutures, can be applied to the entry and exit points. Ice can be applied indirectly to the implantation site to further aid in the healing process.

In embodiments wherein the tissue-penetrating member 21 includes a cutting tip, the passageway can be formed as the tip advances through the volume of tissue and cuts through native tissue. In other embodiments, a pre-formed tract could be provided, and the tissue-penetrating member equipped with a non-cutting (e.g. bullet) tip to traverse the pre-formed tract. In providing a suitable anchor, at least a portion of enlarged head portion 29, in certain aspects, will become wedged in this passage. In some procedures no part of the enlarged head portion will become wedged in the passage.

Implant deployment devices of the invention, especially those incorporating porous or otherwise absorbent implant materials such as ECM or collagenous materials, can advantageously be used with the implant material in a hydrated condition. Hydration can be achieved with any suitable liquid, typically an aqueous medium such as sterile water, saline, or the like. The wetting medium may also include other therapeutic substances, such as antibiotics, anesthetics and/or other pharmaceuticals. Contact between the wetting agent and the implant material can be achieved in any suitable fashion, including immersion such as dipping or soaking, spraying, etc. Further, the wetting agent along with any active ingredients such as antibiotics can be delivered to a portion of the implant internalized in the tissue-penetrating member by wicking and/or through openings 26 in the walls of the needle when present.

When an implant utilized in the invention includes an enlarged head portion, this head portion can be shaped and configured in a variety of manners. In some preferred embodiments, an enlarged head portion will be shaped and sized so as to prevent or at least inhibit the head portion from passing through a volume of patient tissue traversed by the tissue-penetrating member. Illustratively, an enlarged head can include portions that are configured to contact tissue adjacent an opening in the tissue in such a way that the head portion is unable to pass through this opening. Thus, while head portion 29 in this specific illustrative embodiment is generally disc-shaped, many other suitably shaped head portions are contemplated as within the scope of the present invention. These include various three-dimensional shapes having rectilinear and/or curvilinear features. Suitable three-dimensional rectilinear shapes can have any suitable number of sides, and can include, for example, cubes, cuboids, tetrahedrons, prisms, pyramids, wedges, and variations thereof. Suitable three-dimensional curvilinear shapes can include, for example, spheres, spheroids, ellipsoids, cylinders, cones, and any suitable variations thereof (e.g., a segment of a sphere, or a truncated cone, etc.).

When an implant is equipped with an enlarged head portion, this head portion and any other part of the implant (e.g., an implant body portion) may be formed as a single unit (e.g., from an amount of the same material), or alternatively, such implant parts may be formed separately and then combined with one another, for example, using an adhesive, by suturing, using mechanical fastener(s), and/or any other suitable joining means. When device components are formed separately and then combined, the manner in which they are combined may be one that is considered essentially permanent or non-permanent. Illustratively, two implant parts may be held together by an absorbable coupling device (e.g., a 2-0 vicryl suture material), which can then degrade some time after implantation. Other effective ways to assemble two or more implant components will be recognized by those skilled in the art, and therefore, are encompassed by the present invention. When formed separately, any two implant components (e.g., an enlarged head portion and an implant body portion) may or may not be comprised of the same biocompatible material(s). Suitable materials for construction include various naturally derived and non-naturally derived materials as discussed herein.

An inventive implant can include a detachable end portion (e.g., a detachable enlarged head portion). In certain aspects, an implant body and an end portion are formed separately, yet are retained in association with one another, without the use of any other device or material (e.g., sutures, an adhesive, etc.). In such aspects, such device components (e.g., an end segment and an intermediate segment) may be held together by having at least one component (or any portion thereof) received around, through, over, etc., another component (or any portion thereof).

An enlarged head portion such as that shown in FIG. 1, while advantageously included in certain aspects of the invention, is an optional feature of an implant. In some embodiments, an implant that is otherwise similar to that shown in FIG. 1 is provided without an enlarged head portion. These sorts of implants can be shaped and sized to reside wholly or partially inside a deployment member lumen (or other receiving space in the member) to be carried into patient tissue. When an implant is able to be positioned entirely in a deployment member lumen, various means may then be used to retrieve the implant from the lumen. These include inserting a grasping device into the lumen to grasp the implant and pull it from the lumen, as well as incorporating a suture or other similar object into the implant which can be grasped and pulled. Other suitable means will be recognized by those skilled in the art, and therefore, are encompassed by the present invention. Still, in certain forms, an implant that does not have an enlarged head portion will have a segment extending from the deployment member lumen (or other receiving space in the member) when the implant is fully seated in the lumen. When desired, this segment can then be grasped directly by hand in situations where such access is possible, although in some embodiments, grasping this segment will additionally or alternatively involve the use of one or more instruments. An implant of this sort may also incorporate a suture or other similar object that extends from this segment which can be grasped and pulled.

Figure 5:
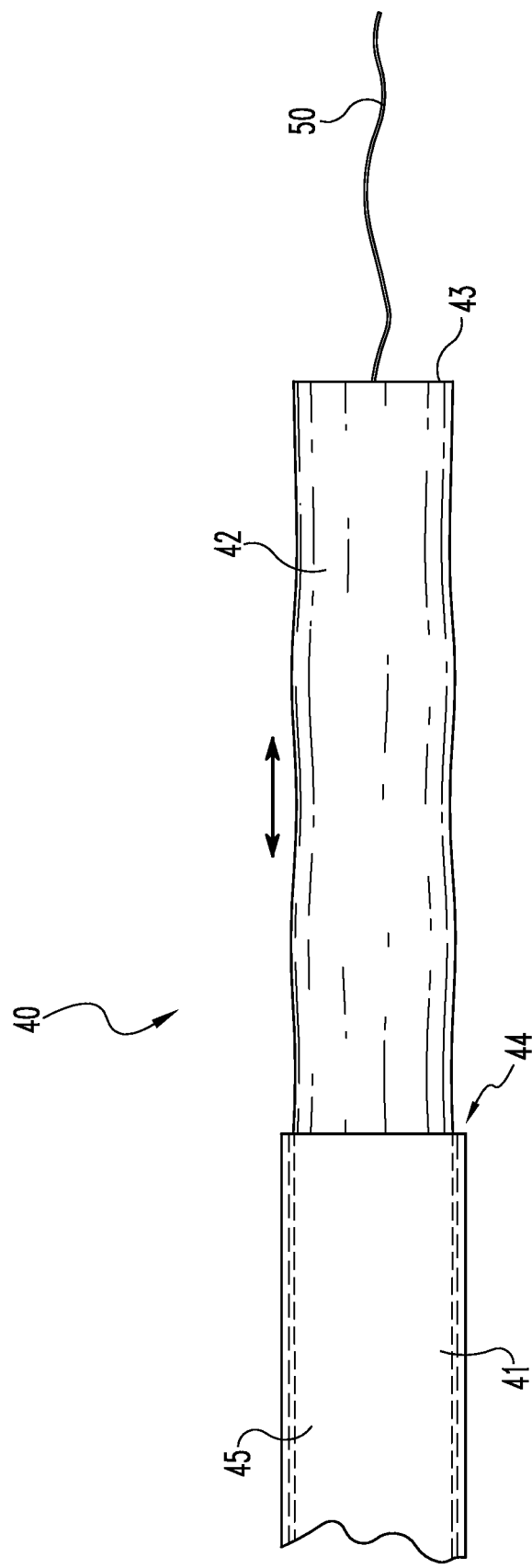
FIG. 5 provides an enlarged, partial view of an implant deployment device according to another embodiment of the present invention.

FIG. 5 is a partial view of another illustrative implant deployment device 40 of the invention. Device 40 includes a tissue-penetrating member 41 and an implant 42. Implant 42, which is generally cylindrical, has a distal end (not shown) and a proximal end 43. Additionally, implant 42 incorporates a tether 50 which extends proximally from its proximal end. Tissue-penetrating member 41 has a leading end (not shown) and a trailing, open end 44. The leading end may be shaped and configured in any suitable manner including any of those described herein. Tissue-penetrating member 41 additionally includes a generally cylindrical wall 45. This wall surrounds a receiving space that communicates with the trailing, open end of the member. This receiving space is configured for receipt of all or part of an implantable object for carrying the object into patient tissue. Accordingly, an implant such as implant 42 can be inserted into the receiving space through the trailing, open end as shown in FIG. 5. While not necessary to broader aspects of the invention, device 40 can be configured so that at least part of implant 42 extends from the trailing, open end when the implant is fully seated in the member.

Device 40 can be used in a variety of manners to introduce implant 42 into patient tissue. As part of one illustrative inventive method, tissue-penetrating member 41 is inserted into a volume of patient tissue through an entry point such that at least part of implant 42 is carried into the volume of patient tissue in the tissue-penetrating member receiving space. Thereafter, tissue-penetrating member 41 is further advanced through the volume of patient tissue until it is forced out of this tissue through an exit point, which is spaced from the aforementioned entry point. Depending on factors such as the length of tissue-penetrating member 41, the distance between the entry point and the exit point, the extent (if any) to which implant 42 is extending out of the tissue-penetrating member receiving space, etc., the proximal end of implant 42 may be positioned at various locations in and/or around the volume of patient tissue when leading end 43 exits the tissue. Thus, in some instances, when the leading end of tissue-penetrating member 41 exits the tissue, the proximal end of implant 42 will be located outside the tissue. In some other instances, when the leading end of tissue-penetrating member 41 exits the tissue, proximal end 43 will be located inside the tissue with tether 50 extending out of the tissue through the entry point. With this sort of arrangement, tether 50 can then be grasped and used to facilitate the placement of implant 42 in the tissue. Illustratively, tether 50 can be held stationary or pulled in a direction generally opposite that of which the tissue-penetrating member is being advanced through the tissue.

Tissue-penetrating member 41 can be advanced through the volume of patient tissue until it exits the tissue entirely. In doing so, a counterforce can be applied to the implant (e.g., by grasping tether 50 and pulling it, holding it stationary, etc.) as the trailing end of the tissue-penetrating member is forced away from the entry point. In some cases, this sort of force will be necessary to help draw the implant out of the tissue-penetrating member through its trailing, open end 44. Tissue-penetrating member 41 can then be fully removed from the tissue and discarded, leaving at least part of implant 42 in the tissue so as to remain there along a passageway traversed by the tissue-penetrating member. If desirable, tether 50 may then be used to adjust the positioning of the implant in the passageway.

In some embodiments, implant 42 will be deployed in the passageway such that it has portions extending out of the tissue through the entry point and/or the exit point. If present, these portions can be cut off and discarded, and then the entry point and the exit point can be closed. A tissue opening can be closed in any suitable manners including some that involve suturing, stapling and/or applying a bonding agent to tissue adjacent the opening. In some forms, suture or other material that is passed through and around tissue adjacent to an opening to close the opening is additionally passed through portions of the implant residing near the opening, which can provide an enhanced anchoring arrangement of the implant in the tissue. In certain aspects, a suture or other similar object will provide a means for manipulating the position of the implant in a volume of tissue, as well as a means for securing the implant to this tissue.

In certain forms, inventive implant devices are particularly configured to maintain their positioning in a volume of patient tissue following delivery. In some instances, this mean that the shape of the device relative to its surroundings at the treatment site provides enhanced anchoring of the device at the site. As well, the shape of a device, in certain aspects, can be caused or allowed to change at the treatment site to provide enhanced seating of the device, for example, through expansion of a device portion, through a change in the spatial relationship of two or more device parts, or through the addition of a device part.

Figure 4:
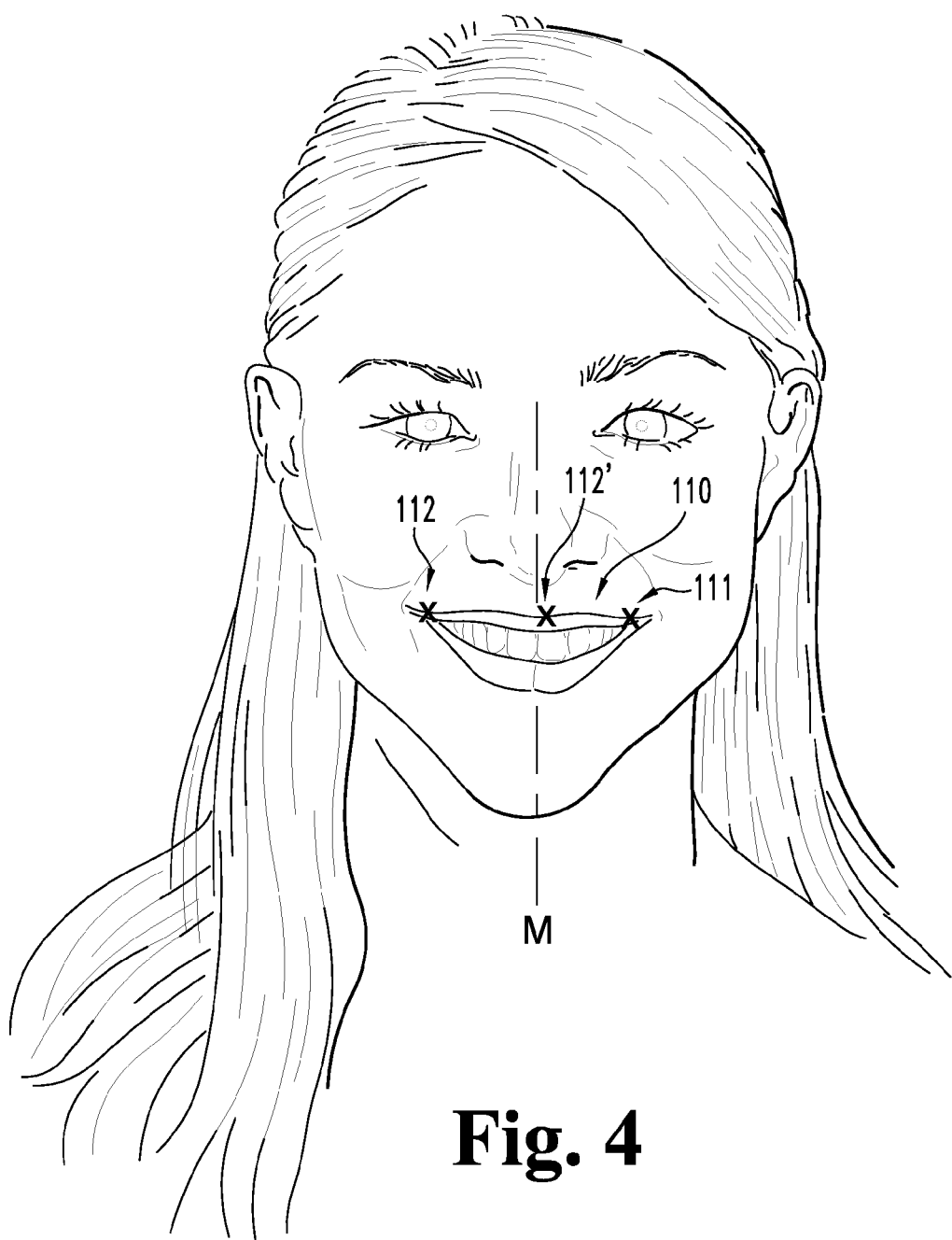
FIG. 4 illustrates a human lip region that can be augmented in accordance with certain aspects of the present invention.

Inventive implant deployment devices can be provided for a variety of purposes including some that involve the augmentation, restoration, etc. of tissue. As illustrated in FIG. 4, a volume of patient tissue to be augmented may occur in and/or around a human upper lip. In this case, the entry point 111 and exit point 112 are located approximately equal distances from the lip's midline M in the mucosal part of the upper lip. Nonetheless, it is understood that the entry point 111 and exit point 112 can be placed in any desired location on or near the lip. Also, there can be more than one entry point 111 and/or more than one exit point 112 in given procedure. For instance, a method may involve augmenting only one side of an upper lip. In this case, a second, alternate exit point 112' is located on the mucosal part of the lip near the lip's midline M (as shown in FIG. 4). Augmenting less than a full lip may be desirable or necessary because of the shape of the lip and/or the nature of the underlying lip tissue. In general, the location of any entry point or exit point may depend on factors, such as but not limited to, the size and shape of the native lip, the extent of augmentation being performed and the desired cosmetic outcome.

It should also be noted that the relative softness and/or diameter of different regions of the implant can be varied to suit a particular procedure, technique, patient, etc. Still further, in certain embodiments, a method of augmenting lip tissue includes prepping the perioral area in a sterile manner and administering a local anesthetic, such as lidocaine with epinephrine, to a lip and/or areas around a lip. Once the implant is implanted in a suitable location, an antibiotic ointment is applied to the punctures at the entry and exit points to reduce the risk of infection. Thereafter, a bandage, or possibly even sutures, are applied to the entry and exit points. Further, ice can be applied indirectly to the implantation site to further aid in the healing process. It will be understood that similar steps of preparing and anesthetizing surgical sites and/or similar post-surgical techniques can be undertaken in other tissue augmentation procedures in accordance with the present invention.

Turning now to a more detailed discussion of materials useful in forming implants useful in the invention, these materials should generally be biocompatible, and in advantageous embodiments, are comprised of a remodelable material. Particular advantage can be provided by implants including a remodelable collagenous material. Such remodelable collagenous materials, whether reconstituted or naturally-derived, can be provided, for example, by collagenous materials isolated from a warm-blooded vertebrate, and especially a mammal. Such isolated collagenous material can be processed so as to have remodelable, angiogenic properties and promote cellular invasion and ingrowth. Remodelable materials may be used in this context to promote cellular growth on, around, and/or within tissues in which an implant is implanted, e.g., in lip tissue and other tissues in the body.

Suitable remodelable materials can be provided by collagenous extracellular matrix (ECM) materials possessing biotropic properties. For example, suitable collagenous materials include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa including small intestinal submucosa, stomach submucosa, urinary bladder submucosa, and uterine submucosa. Collagenous matrices comprising submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567.

Submucosa-containing or other ECM tissue used in the invention is preferably highly purified, for example, as described in U.S. Pat. No. 6,206,931 to Cook et al. Thus, preferred ECM material will exhibit an endotoxin level of less than about 12 endotoxin units (EU) per gram, more preferably less than about 5 EU per gram, and most preferably less than about 1 EU per gram. As additional preferences, the submucosa or other ECM material may have a bioburden of less than about 1 colony forming units (CFU) per gram, more preferably less than about 0.5 CFU per gram. Fungus levels are desirably similarly low, for example less than about 1 CFU per gram, more preferably less than about 0.5 CFU per gram. Nucleic acid levels are preferably less than about 5 μg/mg, more preferably less than about 2 μg/mg, and virus levels are preferably less than about 50 plaque forming units (PFU) per gram, more preferably less than about 5 PFU per gram. These and additional properties of submucosa or other ECM tissue taught in U.S. Pat. No. 6,206,931 may be characteristic of any ECM tissue used in the present invention.

A typical layer thickness for an as-isolated submucosa or other ECM tissue layer used in the invention ranges from about 50 to about 250 microns when fully hydrated, more typically from about 50 to about 200 microns when fully hydrated, although isolated layers having other thicknesses may also be obtained and used. These layer thicknesses may vary with the type and age of the animal used as the tissue source. As well, these layer thicknesses may vary with the source of the tissue obtained from the animal source.

Suitable bioactive agents may include one or more bioactive agents native to the source of the ECM tissue material. For example, a submucosa or other remodelable ECM tissue material may retain one or more growth factors such as but not limited to basic fibroblast growth factor (FGF-2), transforming growth factor beta (TGF-beta), epidermal growth factor (EGF), cartilage derived growth factor (CDGF), and/or platelet derived growth factor (PDGF). As well, submucosa or other ECM materials when used in the invention may retain other native bioactive agents such as but not limited to proteins, glycoproteins, proteoglycans, and glycosaminoglycans. For example, ECM materials may include heparin, heparin sulfate, hyaluronic acid, fibronectin, cytokines, and the like. Thus, generally speaking, a submucosa or other ECM material may retain one or more bioactive components that induce, directly or indirectly, a cellular response such as a change in cell morphology, proliferation, growth, protein or gene expression.

Submucosa-containing or other ECM materials of the present invention can be derived from any suitable organ or other tissue source, usually sources containing connective tissues. The ECM materials processed for use in the invention will typically include abundant collagen, most commonly being constituted at least about 80% by weight collagen on a dry weight basis. Such naturally-derived ECM materials will for the most part include collagen fibers that are non-randomly oriented, for instance occurring as generally uniaxial or multi-axial but regularly oriented fibers. When processed to retain native bioactive factors, the ECM material can retain these factors interspersed as solids between, upon and/or within the collagen fibers. Particularly desirable naturally-derived ECM materials for use in the invention will include significant amounts of such interspersed, non-collagenous solids that are readily ascertainable under light microscopic examination with appropriate staining. Such non-collagenous solids can constitute a significant percentage of the dry weight of the ECM material in certain inventive embodiments, for example at least about 1%, at least about 3%, and at least about 5% by weight in various embodiments of the invention.

The submucosa-containing or other ECM material used in the present invention may also exhibit an angiogenic character and thus be effective to induce angiogenesis in a host engrafted with the material. In this regard, angiogenesis is the process through which the body makes new blood vessels to generate increased blood supply to tissues. Thus, angiogenic materials, when contacted with host tissues, promote or encourage the formation of new blood vessels into the materials. Methods for measuring in vivo angiogenesis in response to biomaterial implantation have recently been developed. For example, one such method uses a subcutaneous implant model to determine the angiogenic character of a material. See, C. Heeschen et al., Nature Medicine 7 (2001), No. 7, 833-839. When combined with a fluorescence microangiography technique, this model can provide both quantitative and qualitative measures of angiogenesis into biomaterials. C. Johnson et al., Circulation Research 94 (2004), No. 2, 262-268.

Further, in addition or as an alternative to the inclusion of such native bioactive components, non-native bioactive components such as those synthetically produced by recombinant technology or other methods (e.g., genetic material such as DNA), may be incorporated into an ECM material. These non-native bioactive components may be naturally-derived or recombinantly produced proteins that correspond to those natively occurring in an ECM tissue, but perhaps of a different species. These non-native bioactive components may also be drug substances. Illustrative drug substances that may be added to materials include, for example, anti-clotting agents, e.g. heparin, antibiotics, anti-inflammatory agents, thrombus-promoting substances such as blood clotting factors, e.g., thrombin, fibrinogen, and the like, and anti-proliferative agents, e.g. taxol derivatives such as paclitaxel. Such non-native bioactive components can be incorporated into and/or onto ECM material in any suitable manner, for example, by surface treatment (e.g., spraying) and/or impregnation (e.g., soaking), just to name a few. Also, these substances may be applied to the ECM material in a premanufacturing step, immediately prior to the procedure (e.g., by soaking the material in a solution containing a suitable antibiotic such as cefazolin), or during or after engraftment of the material in the patient.

Implants useful in the invention can include xenograft material (i.e., cross-species material, such as tissue material from a non-human donor to a human recipient), allograft material (i.e., interspecies material, with tissue material from a donor of the same species as the recipient), and/or autograft material (i.e., where the donor and the recipient are the same individual). Further, any exogenous bioactive substances incorporated into an ECM material may be from the same species of animal from which the ECM material was derived (e.g. autologous or allogenic relative to the ECM material) or may be from a different species from the ECM material source (xenogenic relative to the ECM material). In certain embodiments, ECM material will be xenogenic relative to the patient receiving the graft, and any added exogenous material (s) will be from the same species (e.g. autologous or allogenic) as the patient receiving the graft. Illustratively, human patients may be treated with xenogenic ECM materials (e.g. porcine-, bovine- or ovine-derived) that have been modified with exogenous human material(s) as described herein, those exogenous materials being naturally derived and/or recombinantly produced.

ECM materials used in the invention may be essentially free of additional, non-native crosslinking, or may contain additional crosslinking. Such additional crosslinking may be achieved by photo-crosslinking techniques, by chemical crosslinkers, or by protein crosslinking induced by dehydration or other means. However, because certain crosslinking techniques, certain crosslinking agents, and/or certain degrees of crosslinking can destroy the remodelable properties of a remodelable material, where preservation of remodelable properties is desired, any crosslinking of the remodelable ECM material can be performed to an extent or in a fashion that allows the material to retain at least a portion of its remodelable properties. Chemical crosslinkers that may be used include for example aldehydes such as glutaraldehydes, diimides such as carbodiimides, e.g., 1-ethyl-3-(3-dimethylaminopropyl)carbodiimide hydrochloride, ribose or other sugars, acyl-azide, sulfo-N-hydroxysuccinamide, or polyepoxide compounds, including for example polyglycidyl ethers such as ethyleneglycol diglycidyl ether, available under the trade name DENACOL EX810 from Nagese Chemical Co., Osaka, Japan, and glycerol polyglycerol ether available under the trade name DENACOL EX 313 also from Nagese Chemical Co. Typically, when used, polyglycerol ethers or other polyepoxide compounds will have from 2 to about 10 epoxide groups per molecule.

Turning now to a discussion of drying techniques that can be useful in certain embodiments of the invention, drying by evaporation, or air drying, generally comprises drying a partially or completely hydrated remodelable material by allowing the hydrant to evaporate from the material. Evaporative cooling can be enhanced in a number of ways, such as by placing the material in a vacuum, by blowing air over the material, by increasing the temperature of the material, by applying a blotting material during evaporation, or by any other suitable means or any suitable combination thereof. The amount of void space or open matrix structure within an ECM material that has been dried by evaporation is typically more diminished than, for example, an ECM material dried by lyophilization as described below.

A suitable lyophilization process can include providing an ECM material that contains a sufficient amount of hydrant such that the voids in the material matrix are filled with the hydrant. The hydrant can comprise any suitable hydrant known in the art, such as purified water or sterile saline, or any suitable combination thereof. Illustratively, the hydrated material can be placed in a freezer until the material and hydrant are substantially in a frozen or solid state. Thereafter, the frozen material and hydrant can be placed in a vacuum chamber and a vacuum initiated. Once at a sufficient vacuum, as is known in the art, the frozen hydrant will sublime from the material, thereby resulting in a dry remodelable material.

In alternative embodiments, a hydrated ECM material can be lyophilized without a separately performed pre-freezing step. In these embodiments, a strong vacuum can be applied to the hydrated material to result in rapid evaporative cooling which freezes the hydrant within the ECM material. Thereafter, the frozen hydrant can sublime from the material thereby drying the ECM material. Desirably, an ECM material that is dried via lyophilization maintains a substantial amount of the void space, or open matrix structure, that is characteristic of the harvested ECM material.

Drying by vacuum pressing generally comprises compressing a fully or partially hydrated remodelable material while the material is subject to a vacuum. One suitable method of vacuum pressing comprises placing a remodelable material in a vacuum chamber having collapsible walls. As the vacuum is established, the walls collapse onto and compress the material until it is dry. Similar to evaporative drying, when a remodelable material is dried in a vacuum press, more of the material's open matrix structure is diminished or reduced than if the material was dried by lyophilization.

In certain aspects, the invention utilizes an implant that include a multilaminate material. Such multilaminate materials can include a plurality of ECM material layers bonded together, a plurality of non-ECM materials bonded together, or a combination of one or more ECM material layers and one or more non-ECM material layers bonded together. To form a multilaminate ECM material, for example, two or more ECM segments are stacked, or one ECM segment is folded over itself at least one time, and then the layers are fused or bonded together using a bonding technique, such as chemical cross-linking or vacuum pressing during dehydrating conditions. An adhesive, glue or other bonding agent may also be used in achieving a bond between material layers. Suitable bonding agents may include, for example, collagen gels or pastes, gelatin, or other agents including reactive monomers or polymers, for example cyanoacrylate adhesives. As well, bonding can be achieved or facilitated between ECM material layers using chemical cross-linking agents such as those described above. A combination of one or more of these with dehydration-induced bonding may also be used to bond ECM material layers to one another.

A variety of dehydration-induced bonding methods can be used to fuse together portions of an ECM material. In one preferred embodiment, multiple layers of ECM material are compressed under dehydrating conditions. In this context, the term "dehydrating conditions" is defined to include any mechanical or environmental condition which promotes or induces the removal of water from the ECM material. To promote dehydration of the compressed ECM material, at least one of the two surfaces compressing the matrix structure can be water permeable. Dehydration of the ECM material can optionally be further enhanced by applying blotting material, heating the matrix structure or blowing air, or other inert gas, across the exterior of the compressed surfaces. One particularly useful method of dehydration bonding ECM materials is lyophilization.

Another method of dehydration bonding comprises pulling a vacuum on the assembly while simultaneously employing the vacuum to press the assembly together. Again, this method is known as vacuum pressing. During vacuum pressing, dehydration of the ECM materials in forced contact with one another effectively bonds the materials to one another, even in the absence of other agents for achieving a bond, although such agents can be used while also taking advantage at least in part of the dehydration-induced bonding. With sufficient compression and dehydration, the ECM materials can be caused to form a generally unitary ECM structure.

It is advantageous in some aspects of the invention to perform drying and other operations under relatively mild temperature exposure conditions that minimize deleterious effects upon any ECM materials being used, for example native collagen structures and potentially bioactive substances present. Thus, drying operations conducted with no or substantially no duration of exposure to temperatures above human body temperature or slightly higher, say, no higher than about 38° C., will preferably be used in some forms of the present invention. These include, for example, vacuum pressing operations at less than about 38° C., forced air drying at less than about 38° C., or either of these processes with no active heating—at about room temperature (about 25° C.) or with cooling. Relatively low temperature conditions also, of course, include lyophilization conditions.

Expandable implant portions can be formed with one or more of a variety of materials including some that are naturally derived and some that are non-naturally derived. Illustratively, three-dimensionally stable porous matrix materials, such as resilient foam or sponge form materials, can be incorporated into an implant useful in the invention. Illustrative sponge or foam matrices will generally comprise porous, three-dimensionally stable bodies formed from suitable biocompatible matrix materials. For example, suitable biocompatible matrix materials include naturally-occurring polymers and/or synthetic polymers. More preferred sponge compositions of the invention will comprise collagen as a matrix-forming material, either alone or in combination with one or more other matrix forming materials. In general, sponge matrices useful in certain embodiments of the present invention can be formed by providing a liquid solution or suspension of a matrix-forming material, and causing the material to form a porous three-dimensionally stable structure; however, a sponge or foam material can be formed using any suitable formation method, as is known in the art.

Illustratively, in the formation of a collagenous sponge or foam material, a collagen solution or suspension can be prepared. The collagen may be derived from mammalian or other animal sources, for example, bovine, porcine or human sources, and desirably is derived from remodelable ECM materials as discussed herein. Synthetically-derived collagen may also be used. The determination of suitable collagen concentrations in the solution will be within the purview of those skilled in the art, with concentration ranges of about 0.05 g/ml to about 0.2 g/ml being typical.

Digestion of the collagen to form the collagen solution is usually carried out under acidic conditions, starting with ground, minced or otherwise comminuted collagen-containing tissue. Optionally, enzymatic digestion may be utilized using known enzymes for this purpose such as pepsin, trypsin, and/or papain. After digestion, the enzymes can be removed by suitable, known techniques.

The collagenous solution and/or suspension can be employed as a moldable or castable material in the formation of the foam or sponge. The cast material can be dried directly without chemical crosslinking or can be crosslinked with a suitable crosslinking agent and then dried. Illustrative crosslinking agents for these purposes include glutaraldehyde, formaldehyde, carbodiimides, UV irradiation, or other crosslinking agents. In preferred embodiments of the invention, the crosslinking agent will contain polar groups that impart a hydrophilic character to the final sponge matrix material. Desirably, a polyepoxide crosslinker is utilized for this purpose, especially a polyglycidyl ether compound. Suitable such compounds include ethylene glycol diglycidyl ether, available under the trade name Denacol EX810 from Nagese Chemical Co., Osaka, Japan, and glycerol polyglycidyl ether available under the trade name Denacol EX313 also from Nagese Chemical Co. Typically, polyglycidyl ethers or other polyepoxide compounds utilized in the invention will have from 2 to about 10 epoxide groups per molecule. The use of such epoxides and/or other crosslinking agents which impart polar groups and a hydrophilic character to the resulting matrix will provide for good wettability and rapid hydration and expansion of certain implants useful in the invention.

Preferred sources of collagen for forming sponge matrices useful in certain embodiments of the invention include extracellular matrix materials such as submucosa-containing collagenous tissue materials and other collagenous materials as described elsewhere herein. These include, for example, tissue materials comprising small intestinal submucosa, stomach submucosa, urinary bladder submucosa, liver basement membrane, and other basement membrane materials. For additional information as to these collagenous matrix materials and their preparation, reference can be made, for example, to U.S. Pat. Nos. 4,511,653, 4,902,508, 4,956,178, 5,554,389, and 6,099,567, and International Publication Nos. WO9825637 and WO9822158, each of which is hereby incorporated herein by reference in its entirety. In forming sponge matrices, these materials are preferably processed and utilized under conditions which retain their favorable growth properties. This may include, for example, processing under conditions in which native proteins and/or other materials, for instance biotropic agents, are retained in their bioactive form. For example, the collagen sources, and resulting sponge matrices, may include active native substances such as one or more growth factors, e.g. basic fibroblast growth factor (FGF-2); transforming growth factor beta (TGF-beta); epidermal growth factor (EFG); platelet derived growth factor (PDGF); and/or other substances such as glycosaminoglycans (GAGs); and/or fibronectin (FN).

Sponge matrix materials that can be used to form illustrative implants useful in the invention can be highly expandable when wetted, so as to achieve an expanded configuration. Illustratively, expandable sponge materials can exhibit the capacity to expand at least 100% by volume, more preferably at least about 200% by volume, and typically in the range of about 300% by volume to about 1000% by volume, when wetted to saturation with deionized water. Sponge materials used in the invention can also exhibit advantageous rates of expansion, achieving volume expansions as noted above in less than about 10 seconds, more preferably less than about 5 seconds, when immersed in deionized water.

Highly compact, dense sponge matrices can be prepared by first hydrating or otherwise wetting a porous sponge matrix, and then compressing and drying the element. Such preparative processes generally provide a more dense, rigid and stably compressed sponge matrix than processes such as simple compaction of the dry sponge matrix. Drying can be conducted sufficiently to stabilize the sponge matrix. For example, preferred drying procedures will reduce the liquid (e.g. water) content of the matrix to less than about 20% by weight, more preferably less than about 10% by weight. Compression forces can be applied so as to achieve a final density and/or desirable configuration, and can be applied in one, two or three dimensions, including radially. The drying of the compacted element can involve lyophilization (or freeze drying) or vacuum drying at ambient or elevated temperatures. When processed in this fashion, upon removal of the compaction force, the sponge matrix is stabilized structurally and remains in its highly dense and compacted state until contacted with a liquid susceptible to absorption by the matrix, for example body fluids. The pores of the matrix are thereby stably retained at a volume substantially reduced from their maximum volume, but return to a partially or fully expanded state when the matrix material is wetted.

Compressed sponge matrices used in an implant can be highly dense, typically having densities of at least about 0.05 g/cm3, preferably in the range of about 0.05 g/cm3 to about 0.2 g/cm3, and more preferably about 0.075 g/cm3 to about 0.2 g/cm3. The compacted sponge matrix can have sufficient rigidity to be deployed by passage through needles, catheters or sheaths, for example by utilizing a push rod or other pusher element to force the sponge matrix graft body through the needle and/or catheter cannula. Expanded sponge densities (dry) will generally be less than the corresponding compacted densities. Typical expanded densities (dry) will range from about 0.01 g/cm3 to about 0.1 g/cm3, more preferably about 0.02 g/cm3 to about 0.07 g/cm3.

Compressed sponge materials may also contain agents which promote further retention of the compressed, high density form of the matrices. These may include for example starch, cellulose, sugars such as dextrose, or glycerin. Such agents can optionally be included in the liquid (preferably aqueous) used to hydrate or otherwise wet the sponge prior to compaction and drying. For additional information concerning foam or sponge form materials that can be useful in certain embodiments of the present invention, reference can be made, for example, to U.S. Pat. App. Pub. No. 2003/0013989.

In additional embodiments, graft constructs useful in the invention can include ECM materials and other collagenous materials that have been subjected to processes that expand the materials. Illustratively, an expanded remodelable collagenous implant can be formed and placed within a cannulated device, such as depicted by implant 22 in FIG. 1. In certain forms, such expanded materials can be formed by the controlled contact of an ECM material with one or more alkaline substances until the material expands, and the isolation of the expanded material. Illustratively, the contacting can be sufficient to expand the ECM material to at least 120% of (i.e. 1.2 times) its original bulk volume, or in some forms to at least about two times its original volume. Thereafter, the expanded material can optionally be isolated from the alkaline medium, e.g. by neutralization and/or rinsing. The collected, expanded material can be used in any suitable manner in the preparation of an implant useful in certain aspects of the invention. Illustratively, the expanded material can be enriched with bioactive components, dried, and/or molded, etc., in the formation of a desirably shaped and configured graft construct. In certain embodiments, a dried graft body formed with the expanded ECM material can be highly compressible (or expandable) such that the material can be compressed for delivery, such as into a body space to be augmented, and thereafter expand upon placement therein, so as to become anchored within the space (e.g., within a passageway or other similar space in the body) and/or cause closure of the space.

Expanded collagenous or ECM materials can be formed by the controlled contact of a collagenous or ECM material with an aqueous solution or other medium containing sodium hydroxide. Alkaline treatment of the material can cause changes in the physical structure of the material that in turn cause it to expand. Such changes may include denaturation of the collagen in the material. In certain embodiments, it is preferred to expand the material to at least about three, at least about four, at least about 5, or at least about 6 or even more times its original bulk volume. The magnitude of the expansion is related to several factors, including for instance the concentration or pH of the alkaline medium, exposure time, and temperature used in the treatment of the material to be expanded.

ECM materials that can be processed to make expanded materials can include any of those disclosed herein or other suitable ECM's. Typical such ECM materials will include a network of collagen fibrils having naturally-occurring intramolecular cross links and naturally-occurring intermolecular cross links. Upon expansion processing as described herein, the naturally-occurring intramolecular cross links and naturally-occurring intermolecular cross links can be retained in the processed collagenous matrix material sufficiently to maintain the collagenous matrix material as an intact collagenous sheet material; however, collagen fibrils in the collagenous sheet material can be denatured, and the collagenous sheet material can have an alkaline-processed thickness that is greater than the thickness of the starting material, for example at least 120% of the original thickness, or at least twice the original thickness.

Illustratively, the concentration of the alkaline substance for treatment of the remodelable material can be in the range of about 0.5 M to about 4 M, with a concentration of about 1 M to about 3 M being more preferable. Additionally, the pH of the alkaline substance can in certain embodiments range from about 8 to about 14. In preferred aspects, the alkaline substance will have a pH of from about 10 to about 14, and most preferably of from about 12 to about 14.

In addition to concentration and pH, other factors such as temperature and exposure time will contribute to the extent of expansion, as discussed above. In this respect, in certain variants, the exposure of the collagenous material to the alkaline substance is performed at a temperature of about 4 to about 45° C. In preferred embodiments, the exposure is performed at a temperature of about 25 to about 40° C., with 37° C. being most preferred. Moreover, the exposure time can range from at least about one minute up to about 5 hours or more. In some embodiments, the exposure time is about 1 to about 2 hours. In a particularly preferred embodiment, the collagenous material is exposed to a 3 M solution of NaOH having a pH of 14 at a temperature of about 37° C. for about 1.5 to 2 hours. Such treatment results in collagen denaturation and a substantial expansion of the remodelable material. Denaturation of the collagen matrix of the material can be observed as a change in the collagen packing characteristics of the material, for example a substantial disruption of a tightly bound collagenous network of the starting material. A non-expanded ECM or other collagenous material can have a tightly bound collagenous network presenting a substantially uniform, continuous surface when viewed by the naked eye or under moderate magnification, e.g. 100× magnification. Conversely, an expanded collagenous material can have a surface that is quite different, in that the surface is not continuous but rather presents collagen strands or bundles in many regions that are separated by substantial gaps in material between the strands or bundles when viewed under the same magnification, e.g. about 100×. Consequently, an expanded collagenous material typically appears more porous than a corresponding non-expanded collagenous material. Moreover, in many instances, the expanded collagenous material can be demonstrated as having increased porosity, e.g. by measuring for an increased permeability to water or other fluid passage as compared to the non-treated starting material. The more foamy and porous structure of an expanded ECM or other collagenous material can allow the material to be cast or otherwise prepared into a variety of sponge or foam shapes for use in the preparation of implants useful in certain aspects of the invention. It can further allow for the preparation of constructs that are highly compressible and which expand after compression. Such properties can be useful, for example, when the prepared implant construct is to be compressed and loaded into a deployment device (e.g. a lumen of a tissue-penetrating member) for delivery into a volume of patient tissue, and thereafter deployed to expand at the implant site. After such alkaline treatments, the material can be isolated from the alkaline medium and processed for further use. Illustratively, the collected material can be neutralized and/or rinsed with water to remove the alkalinity from the material, prior to further processing of the material to form an implant or implant component.

A starting ECM material (i.e., prior to treatment with the alkaline substance) can optionally include a variety of bioactive or other non-collagenous components including, for example, growth factors, glycoproteins, glycosaminoglycans, proteoglycans, nucleic acids, and lipids. Treating the material with an alkaline substance may reduce the quantity of one, some or all of such non-collagenous components contained within the material. In certain embodiments, controlled treatment of the remodelable material with an alkaline substance will be sufficient to create a remodelable collagenous material which is substantially devoid of nucleic acids and lipids, and potentially also of growth factors, glycoproteins, glycosaminoglycans, and proteoglycans In certain embodiments, one or more bioactive components, exogenous or endogenous, for example, similar to those removed from an expanded material during alkaline processing, can be returned to the material. For example, an expanded material can include a collagenous material which has been depleted of nucleic acids and lipids, but which has been replenished with growth factors, glycoproteins, glycosaminoglycans, and/or proteoglycans. These bioactive components can be returned to the material by any suitable method. For instance, in certain forms a tissue extract, such as is discussed in U.S. Pat. No. 6,375,989 which is hereby incorporated herein by reference in its entirety, containing these components can be prepared and applied to an expanded collagenous material. In one embodiment, the expanded collagenous material can be incubated in a tissue extract for a sufficient time to allow bioactive components contained therein to associate with the expanded collagenous material. The tissue extract may, for example, be obtained from non-expanded collagenous tissue of the same type used to prepare the expanded material. Other means for returning or introducing bioactive components to an expanded remodelable collagenous material include spraying, impregnating, dipping, etc. as known in the art. By way of example, an expanded collagenous material may be modified by the addition of one or more growth factors such as basic fibroblast growth factor (FGF-2), transforming growth factor beta (TGF beta), epidermal growth factor (EGF), platelet derived growth factor (PDGF), and/or cartilage derived growth factor (CDGF). As well, other biological components may be added to an expanded collagenous material, such as heparin, heparin sulfate, hyaluronic acid, fibronectin and the like. Thus, generally speaking, an expanded collagenous material may include a bioactive component that induces, directly or indirectly, a cellular response such as a change in cell morphology, proliferation, growth, protein or gene expression.

Expanded collagenous materials can be used in preparing a wide variety of implants useful in the invention. Methods for preparing such implants can include contacting an ECM or other collagenous starting material with an alkaline substance in an amount effective to expand the material, comminuting the expanded material e.g., with a blender, casting or otherwise forming the blended expanded collagenous material into an implant or implant component shape (e.g. one of those described herein), and lyophilizing the expanded material to form a dried construct. Alternatively, one or more sheets of an expanded remodelable collagenous material can be formed. In one embodiment, one or more sheets of an expanded remodelable collagenous material can be stacked, frozen and lyophilized to form a multi-laminate expanded remodelable collagenous material. One or more sheets can be rolled to form a generally cylindrical implant, if desired.

In one particularly preferred embodiment, an implant prepared from a sponge form expanded remodelable collagenous material can be compressed (e.g., by hand) and loaded into a tissue-penetrating member. Such an implant can be formed by casting the expanded material into a generally cylindrical mold followed by lyophilization. Alternatively, a sheet-form material can be prepared by forming one or more sheets of an expanded remodelable collagenous material and rolling the one or more sheets to form a generally cylindrical implant. Either processing method can result in an implant that can be compressed and loaded into a tissue-penetrating member. The tissue-penetrating member is preferably a needle that has a lumen extending longitudinally therethrough. The lumen is configured to receive the compressed expanded remodelable collagenous material and to retain the material in a compressed condition until the material is deployed from the penetrating member. The expanded remodelable collagenous material can also include an interface with a suture, button or other similar feature to allow it to be withdrawn from the tissue-penetrating member during implantation. After the expanded remodelable collagenous material is delivered, the material can expand from its compressed state to provide a soft, natural-looking bulk to a patient's face.

Additionally, in certain aspects, an expandable implant portion includes one or more adaptations for enhancing expansion of external features of the implant in a tissue passage. Such adaptations can include one or more perforations, cuts, channels, indentations, scores, etc. in the implant body. These and other adaptations for enhancing the expansive ability of the implant in a tissue passage will be recognized by the skilled artisan and are encompassed by the present invention.

As well, implants useful in the present invention may be comprised of biocompatible materials derived from a number of biological polymers, which can be naturally occurring or the product of in vitro fermentation, recombinant genetic engineering, and the like. Purified biological polymers can be appropriately formed into a substrate by techniques such as weaving, knitting, casting, molding, and extrusion. Suitable biological polymers include, without limitation, collagen, elastin, keratin, gelatin, polyamino acids, polysaccharides (e.g., cellulose and starch) and copolymers thereof.

Useful implants can also include one or more of a variety of synthetic polymeric materials including but not limited to bioresorbable and/or non-bioresorbable plastics. Bioresorbable, or bioabsorbable polymers that may be used include, but are not limited to, poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, and polyphosphazenes. These or other bioresorbable materials may be used, for example, where only a temporary blocking or closure function is desired, and/or in combination with non-bioresorbable materials where only a temporary participation by the bioresorable material is desired.

Non-bioresorbable, or biostable polymers that may be used include, but are not limited to, polytetrafluoroethylene (PTFE) (including expanded PTFE), polyethylene terephthalate (PET), polyurethanes, silicones, and polyesters and other polymers such as, but not limited to, polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; and rayon-triacetate.

In some forms, the tissue-penetrating member itself will be considered lubricious by those skilled in the art, while in other embodiments, it will be coated or otherwise prepared to give it lubricious properties. Such a coating or other outer layer may be applied (e.g., by spraying, dip coating, over-extruding or by any other suitable means) to the tissue-penetrating member, and may be comprised of a hydrophilic material such as but not limited to parylene or PTFE. In certain aspects, UV (ultra-violet light)-curable, radiation-curable, photoreactive, photoimmobilizing, and other similar coatings are used. These coatings have in common at least one photoreactive species. Coatings can be made from these species, and then all or a portion of a tissue-penetrating member can be coated and the coating cured. Lubricous coating materials include those commercially available from SurModics, Inc., Eden Prairie, Minn., under the trade mark "PhotoLink™."

Additionally, any part of an implant deployment device (e.g., the implant, a coating on the tissue-penetrating member, etc.) can incorporate an effective amount of one or more antimicrobial agents or therapeutic agents otherwise useful to inhibit the population of the implant or surrounding tissue with bacteria or other deleterious microorganisms. Illustrative such agents can include, for example, antibiotics such as penicillin, tetracycline, chloramphenicol, minocycline, doxycycline, vancomycin, bacitracin, kanamycin, neomycin, gentamycin, erythromycin and cephalosporins. Examples of cephalosporins include cephalothin, cephapirin, cefazolin, cephalexin, cephradine, cefadroxil, cefamandole, cefoxitin, cefaclor, cefuroxime, cefonicid, ceforanide, cefotaxime, moxalactam, ceftizoxime, ceftriaxone, and cefoperazone, and antiseptics (substances that prevent or arrest the growth or action of microorganisms, generally in a nonspecific fashion) such as silver sulfadiazine, chlorhexidine, glutaraldehyde, peracetic acid, sodium hypochlorite, phenols, phenolic compounds, iodophor compounds, quaternary ammonium compounds, and chlorine compounds. These or other therapeutic agents, can be incorporated directly on or in an implant and/or other device component, or they can be incorporated with a suitable binder or carrier material, including for instance hydrogel materials. The carrier or binder coating can be applied to a device component by any suitable means including, for example, spraying, dipping, etc. as known in the art. The antimicrobial or other therapeutic agent can be added to the carrier/binder coating either prior to or after application of the coating to the device component.

Additionally, the present invention provides kits that include products as described herein for augmentation and other purposes, e.g., in sterile medical packaging. The kits can include written materials including instructions for delivering and/or otherwise using the products for augmentation and other purposes, e.g., to augment lips or other facial tissue as described herein. Related embodiments of the invention include methods for distributing such products for augmentation and other purposes, or otherwise conducting business, which include distributing such products for augmentation and other purposes, and also distributing information relating the use of such products for augmentation and other purposes. Such information can be distributed packaged with the products for augmentation and other purposes, or separately, e.g., including information or instructions available on a communication network, including a global computer communication network such as the internet.

Some embodiments of the invention provide a line of medical kits, wherein a medical kit of the invention includes one or more products of the invention in a sealed package. In some forms of the invention, medical kits are provided that include one or more products for augmentation and other purposes such as any of those described herein, and potentially also suitable instrumentation to be used in the introduction of an implant into patient tissue, enclosed within sterile medical packaging. Illustratively, such a medical product can have packaging including a backing layer and a front film layer that are joined by a boundary of pressure-adhesive as is conventional in medical packaging, wherein the contents of the packaging are sealed between the backing layer and front film layer. Sterilization of such a medical product may be achieved, for example, by irradiation, ethylene oxide gas, or any other suitable sterilization technique, and the materials and other properties of the medical packaging will be selected accordingly. Additionally, the packaging can include indicia to communicate the contents of the package to a person, machine, computer, and/or electronic device. Such indicia may include the dimensions of, the type of materials used to form, and/or other useful information relating to the contents of the package.

All publications and patent applications cited in this specification are herein incorporated by reference as if each individual publication or patent application were specifically and individually indicated to be incorporated by reference. Further, any theory, mechanism of operation, proof, or finding stated herein is meant to further enhance understanding of the present invention, and is not intended to limit the present invention in any way to such theory, mechanism of operation, proof, or finding. While the invention has been illustrated and described in detail in the drawings and foregoing description, the same is to be considered as illustrative and not restrictive in character, it being understood that only selected embodiments have been shown and described and that all equivalents, changes, and modifications that come within the spirit of the inventions as defined herein or by the following claims are desired to be protected.

What is claimed is:

1. A device for introducing an implant into soft tissue of a patient, the device comprising:
    a tissue-penetrating member configured to enter a volume of patient tissue through an entry point and to exit said volume of patient tissue through an exit point spaced from said entry point, said tissue-penetrating member having a leading end and a trailing end and providing a receiving space for receipt of an implant body portion for carrying said implant body portion into said volume of patient tissue;
    an implant having an implant body portion removably received in said receiving space and configured for deployment from said receiving space in said volume of patient tissue so as to remain deployed in said volume of patient tissue along a passageway traversed by said tissue-penetrating member; and
    wherein said implant includes an enlarged head portion configured to remain external of said receiving space and being sized and shaped to inhibit passage of the enlarged head portion through said volume of patient tissue.

2. The device of claim 1, wherein said trailing end provides an opening in communication with said receiving space.

3. The device of claim 2, wherein said implant body portion is configured for deployment from said receiving space through said trailing open end.

4. The device of claim 1, wherein said implant body portion is removably secured within said receiving space.

5. The device of claim 1, wherein said implant body portion is shaped and sized to fill the entire receiving space.

6. The device of claim 1, wherein said receiving space extends the entire distance between said leading end and said trailing end.

7. The device of claim 6, wherein said implant body portion is shaped and sized to fill the entire receiving space.

8. The device of claim 1 further comprising a filament extending from said implant.

9. The device of claim 1, wherein said implant body portion is comprised of a rolled sheet-form material.

10. The device of claim 1, wherein the implant body portion is comprised of a remodelable material.

11. The device of claim 1, wherein the implant body portion is comprised of a collagen-containing material.

12. The device of claim 1, wherein the implant body portion is comprised of an extracellular matrix material.

13. The device of claim 12, wherein the extracellular matrix material comprises submucosa, serosa, pericardium, dura mater, peritoneum, or dermal collagen.

14. The device of claim 1, wherein the implant body portion is comprised of a synthetic polymeric material.

15. A method for introducing an implant into a volume of patient tissue, the method comprising:
    passing the tissue-penetrating member of the device according to claim 1 through a volume of patient tissue, wherein said tissue-penetrating member enters said volume of patient tissue through an entry point and exits said volume of patient tissue through an exit point spaced from said entry point, and wherein said implant body portion is carried into said volume of patient tissue in said receiving space and is deployed from said receiving space in said volume of patient tissue so as to remain deployed in said volume of patient tissue along a passageway traversed by said tissue-penetrating member.

16. The method of claim 15, wherein said volume of patient tissue includes human facial tissue.

17. The method of claim 15, wherein said volume of patient tissue includes human lip tissue.

18. A device for introducing an implant into soft tissue of a patient, the device comprising:
    a tissue-penetrating member configured to pass in its entirety through a volume of patient tissue and having a lumen communicating with a trailing open end, said lumen configured for receipt of an implant body portion for carrying said implant body portion into said volume of patient tissue;
    an implant having an implant body portion removably received in said lumen and suitable for deployment from said lumen in said volume of patient tissue and through said trailing open end so as to remain deployed in said volume of patient tissue along a passageway traversed by said tissue-penetrating member; and
    wherein said implant includes an enlarged head portion configured to remain external of said lumen and being sized and shaped to inhibit passage of the enlarged head portion through said volume of patient tissue.

19. A method for introducing an implant into a volume of patient tissue, the method comprising:
    passing the tissue-penetrating member of the device according to claim 18 in its entirety through a volume of patient tissue, wherein said implant body portion is carried into said volume of patient tissue in said lumen and is deployed from said lumen in said volume of patient tissue and through said trailing open end so as to remain deployed in said volume of patient tissue along a passageway traversed by said tissue-penetrating member.

20. A method for introducing an implant into a volume of patient tissue, the method comprising:
inserting the tissue-penetrating member of the device according to claim 18 into said volume of patient tissue through an entry point such that said implant body portion is carried into said volume of patient tissue; and
forcing said tissue-penetrating member out of said volume of patient tissue through an exit point spaced from said entry point, wherein said enlarged head portion makes contact with patient tissue adjacent said entry point, said contact effective to anchor said implant in said volume of patient tissue such that said implant body portion is drawn from said lumen as said trailing open end is forced away from said entry point.

* * * * *